US012458765B1

(12) United States Patent
Kaczkowski

(10) Patent No.: US 12,458,765 B1
(45) Date of Patent: Nov. 4, 2025

(54) FLUID INHALATION DEVICE

(71) Applicant: Kaczkowski, Inc., Little Rock, AR (US)

(72) Inventor: Michael D. Kaczkowski, Little Rock, AR (US)

(73) Assignee: Kaczkowski, Inc., Little Rock, AR (US)

( * ) Notice: Subject to any disclaimer, the term of this patent is extended or adjusted under 35 U.S.C. 154(b) by 0 days.

(21) Appl. No.: 19/065,937

(22) Filed: Feb. 27, 2025

Related U.S. Application Data

(63) Continuation of application No. 18/984,287, filed on Dec. 17, 2024.

(51) Int. Cl.
*A61M 11/02* (2006.01)
*A24F 42/20* (2020.01)
*A24F 42/60* (2020.01)

(52) U.S. Cl.
CPC ............. *A61M 11/02* (2013.01); *A24F 42/20* (2020.01); *A24F 42/60* (2020.01)

(58) Field of Classification Search
CPC .... A61M 11/002; A61M 11/06; A61M 15/00; A61M 15/0036; A61M 15/0041; A61M 15/0045; A61M 15/0051; A61M 15/0055; A61M 15/0085; A61M 15/0091; A61M 15/0093; A61M 16/1085; A61M 16/125; A61M 16/16; A61M 2202/064; A61M 2205/0233; A61M 2205/073; A61M 2205/8206; A61M 2209/082; A61M 2209/084; B05B 1/265; B05B 14/00; B05B 7/0012; B05B 7/2429; B05B 7/2435; Y10S 261/65
See application file for complete search history.

(56) References Cited

U.S. PATENT DOCUMENTS 3,097,645 A * 7/1963 Lester .................... A61M 11/06
239/338
4,054,622 A * 10/1977 Lester .................... A61M 11/06
261/78.2
4,251,033 A * 2/1981 Rich ..................... B05B 7/0012
261/78.2
4,284,089 A 8/1981 Ray
4,588,129 A * 5/1986 Shanks .................. A61M 11/06
239/338
D299,066 S 12/1988 Newell et al.
4,792,097 A * 12/1988 Kremer, Jr. ........... B05B 7/0012
261/78.2
4,793,366 A 12/1988 Hill
4,800,903 A 1/1989 Ray et al.
4,917,120 A 4/1990 Hill
(Continued)

*Primary Examiner* — Annette Dixon
(74) *Attorney, Agent, or Firm* — EVAN LAW GROUP LLC

(57) ABSTRACT

A fluid inhalation device, comprises a casing having therein a fluid reservoir, a fluid-air outlet connected to a top end of the fluid reservoir, a vacuum channel, having a bottom end connected to a bottom end of the fluid reservoir, an air duct, having an air inlet at a first air duct end, and a nozzle connected to a second air duct end through a nozzle throat, and connected to the fluid reservoir through a nozzle exit. The nozzle throat is narrower than the nozzle exit, and a top end of the vacuum channel is connected to the nozzle.

25 Claims, 10 Drawing Sheets

(56) References Cited

U.S. PATENT DOCUMENTS

| | | | | | |
|---|---|---|---|---|---|
| 5,054,477 | A * | 10/1991 | Terada | A61M 16/125 | 128/200.22 |
| 5,167,242 | A | 12/1992 | Turner et al. | | |
| 5,388,574 | A * | 2/1995 | Ingebrethsen | A61M 15/0085 | 128/203.26 |
| 5,400,808 | A | 3/1995 | Turner et al. | | |
| 5,533,497 | A * | 7/1996 | Ryder | B05B 7/0012 | 261/78.2 |
| 6,089,228 | A * | 7/2000 | Smith | A61M 15/0045 | 128/203.15 |
| D514,222 | S | 1/2006 | Anderson et al. | | |
| D660,956 | S | 5/2012 | Zuyderhoudt | | |
| D661,795 | S | 6/2012 | Clarke et al. | | |
| D681,267 | S | 4/2013 | Touzjian | | |
| D721,972 | S | 2/2015 | Brewer et al. | | |
| D762,003 | S | 7/2016 | Lomeli | | |
| D788,697 | S | 6/2017 | Verleur et al. | | |
| D801,579 | S | 10/2017 | Nyaggah | | |
| D801,581 | S | 10/2017 | Scott et al. | | |
| D808,073 | S | 1/2018 | Leidel | | |
| D844,235 | S | 3/2019 | Cividi | | |
| D850,711 | S | 6/2019 | He et al. | | |
| D854,741 | S | 7/2019 | Smith | | |
| D869,085 | S | 12/2019 | Campbell et al. | | |
| D903,937 | S | 12/2020 | Chimbuya et al. | | |
| D984,730 | S | 4/2023 | Boham et al. | | |
| D985,187 | S | 5/2023 | Boham et al. | | |
| 11,772,109 | B2 * | 10/2023 | Zarfl | B05B 7/2435 | 239/124 |
| 2003/0136399 | A1 * | 7/2003 | Foley | A61M 11/002 | 128/200.14 |
| 2023/0263970 | A1 * | 8/2023 | Kaczkowski | B05B 7/2489 | |
| 2023/0264214 | A1 * | 8/2023 | Kaczkowski | A61M 11/06 | |

* cited by examiner

FLUID INHALATION DEVICE

BACKGROUND

A variety of devices are known for atomizing and propelling a liquid. Examples include spray pump bottles, such as those which use an internal propellant (for example spray paint cans, hair sprays, air fresheners and inhalers for asthma medications), or which include a hand pump (hand pump bottles used for window glass cleaning and fabric stain removers). Some devices, such as nicotine vaping devices (E-cigarettes) use heat to vaporize a fluid, that may form an aerosol, which is then inhaled by a user. A nebulizer, a device for producing a fine spray of liquid, and used for inhaled medication, are often powered by compressed air, either from a compressed gas tank or produced using an electric pump.

Examples of such a device powered by compressed gas include those described in U.S. Pat. App., Pub. Nos. 20230264214 and 20230263970, both of which describe cartridges for fluid dispersal. The cartridge is configured to be powered by compress air. In this device a liquid in a liquid reservoir is pulled into a stream of fast flowing air, atomizing the liquid into droplets, and then the droplets travel through a channel and out into the ambient air surrounding a user. A collection of these cartridges may be set up in a base which supplies the compressed air, allowing for a system to control exactly which cartridges received the compressed air, and when the compressed air is received. This allows the system to provide different scents and botanical extract into the ambient air to surround one or more users.

An example of such a device is illustrated in FIG. 1, which illustrates a cross-section interior view. FIG. 1 illustrates a cartridge having a hard casing with an air inlet B and an atomization outlet C. A fluid reservoir D within the hard casing is configured to hold the fluid L therein, and a vacuum channel E connected to the fluid reservoir D at a bottom connection point I and an air duct F at a top connection point J allows a portion of the fluid L to encounter the stream of fast-moving air K. The air duct F moves air K having an initial velocity from the base end of the cartridge towards a choke point G of the air duct F located towards the top end of the cartridge. The choke point G of the air duct F is a point in which the air duct F narrows, resulting in a lower cross-sectional area of the air duct F. In operation, atomized fluid A exits the atomization outlet C when air of sufficiently high pressure enters air inlet B. A reservoir hole H allows atomized fluid A that collects within the air duct F and around atomization outlet C to flow back into the reservoir so that it does not block the air duct F.

SUMMARY

The present invention includes a first variation of a fluid inhalation device, comprising a casing having therein a fluid reservoir, a fluid-air outlet connected to a top end of the fluid reservoir, a vacuum channel, having a bottom end connected to a bottom end of the fluid reservoir, an air duct, having an air inlet at a first air duct end, and a nozzle connected to a second air duct end through a nozzle throat, and connected to the fluid reservoir through a nozzle exit, and a mouth piece, containing the fluid-air outlet. The nozzle throat is narrower than the nozzle exit, and a top end of the vacuum channel is connected to the nozzle.

The present invention includes a second variation of a fluid inhalation device, comprising a casing having therein a fluid reservoir, a fluid-air outlet connected to a top end of the fluid reservoir, a vacuum channel, having a bottom end connected to a bottom end of the fluid reservoir, an air duct, having an air inlet at a first air duct end, and a nozzle connected to a second air duct end through a nozzle throat, and connected to the fluid reservoir through a nozzle exit. The nozzle exit directly opens into the fluid reservoir, the nozzle throat is narrower than the nozzle exit, and a top end of the vacuum channel is connected to the nozzle.

The present invention includes a third variation of a fluid inhalation device, comprising a casing having therein a fluid reservoir, a fluid-air outlet connected to a top end of the fluid reservoir, a vacuum channel, having a bottom end connected to a bottom end of the fluid reservoir, an air duct, having an air inlet at a first air duct end, and a nozzle connected to a second air duct end through a nozzle throat, and connected to the fluid reservoir through a nozzle exit. The nozzle throat is narrower than the nozzle exit, a top end of the vacuum channel is connected to the nozzle, and the fluid inhalation device is configured for human mouth powered operation.

The present invention includes a fourth variation of a fluid inhalation device, comprising a casing having therein a fluid reservoir, a fluid-air outlet connected to a top end of the fluid reservoir, a vacuum channel, having a bottom end connected to a bottom end of the fluid reservoir, an air duct, having an air inlet at a first air duct end, a nozzle connected to a second air duct end through a nozzle throat, and connected to the fluid reservoir through a nozzle exit, a spray shield, between the nozzle exit and the fluid-air outlet, and a fluid-air mixture channel connecting the fluid reservoir to the fluid-air outlet. The nozzle throat is narrower than the nozzle exit, a top end of the vacuum channel is connected to the nozzle, and the nozzle exit directly opens into the fluid-air mixture channel.

The present invention includes a fifth variation, which is a set for assembling a fluid inhalation device, comprising (I) a removable reservoir, including (i) 0.5 to 5 ml of a fluid, and (ii) a breakable seal, maintaining the fluid within the removable reservoir, and (II) a removable top, including a fluid-air outlet. The removable reservoir and the removable top are adapted to attach together to form the fluid inhalation device and configured to break the breakable seal when attached together. The fluid inhalation device comprises a casing having therein a fluid reservoir, a fluid-air outlet connected to a top end of the fluid reservoir, a vacuum channel, having a bottom end connected to a bottom end of the fluid reservoir, an air duct, having an air inlet at a first air duct end, and a nozzle connected to a second air duct end through a nozzle throat, and connected to the fluid reservoir through a nozzle exit. The nozzle throat is narrower than the nozzle exit, and a top end of the vacuum channel is connected to the nozzle.

The present invention includes a sixth variation of a fluid inhalation device, comprising a fluid reservoir, means for producing a fluid-air mixture, means for providing a stream of air into the device, means for returning large droplets and bulk fluid from the fluid-air mixture to the fluid reservoir, a fluid-air outlet, and means for providing the fluid-air mixture to the fluid-air outlet.

DEFINITIONS

"Connected" and "connects" means fluidly connected or fluidly connects, respectively, which allow for the flow of fluids, including gases (such as air) and liquids (such as water, ethanol and liquid mixtures, solutions, dispersions, suspensions and emulsions).

"Nozzle" means a channel or chamber where air may mix with another fluid, to form a fluid-air mixture.

The spatial prepositions such as "top," "bottom," "above," and "below" which describe the relative position of structural elements in space, are in reference to the orientation of the device (such as the fluid inhalation device) during use. For example, during use the fluid inhalation device is always oriented with the fluid reservoir bottom end below the remainder of the fluid reservoir.

The phrase "configured for human mouth powered operation" means operated by suction by mouth on a mouth piece at a pressure of −0.14 to −0.36 PSI, negative pressure relative to atmospheric pressure.

DETAILED DESCRIPTION

Figure 1:
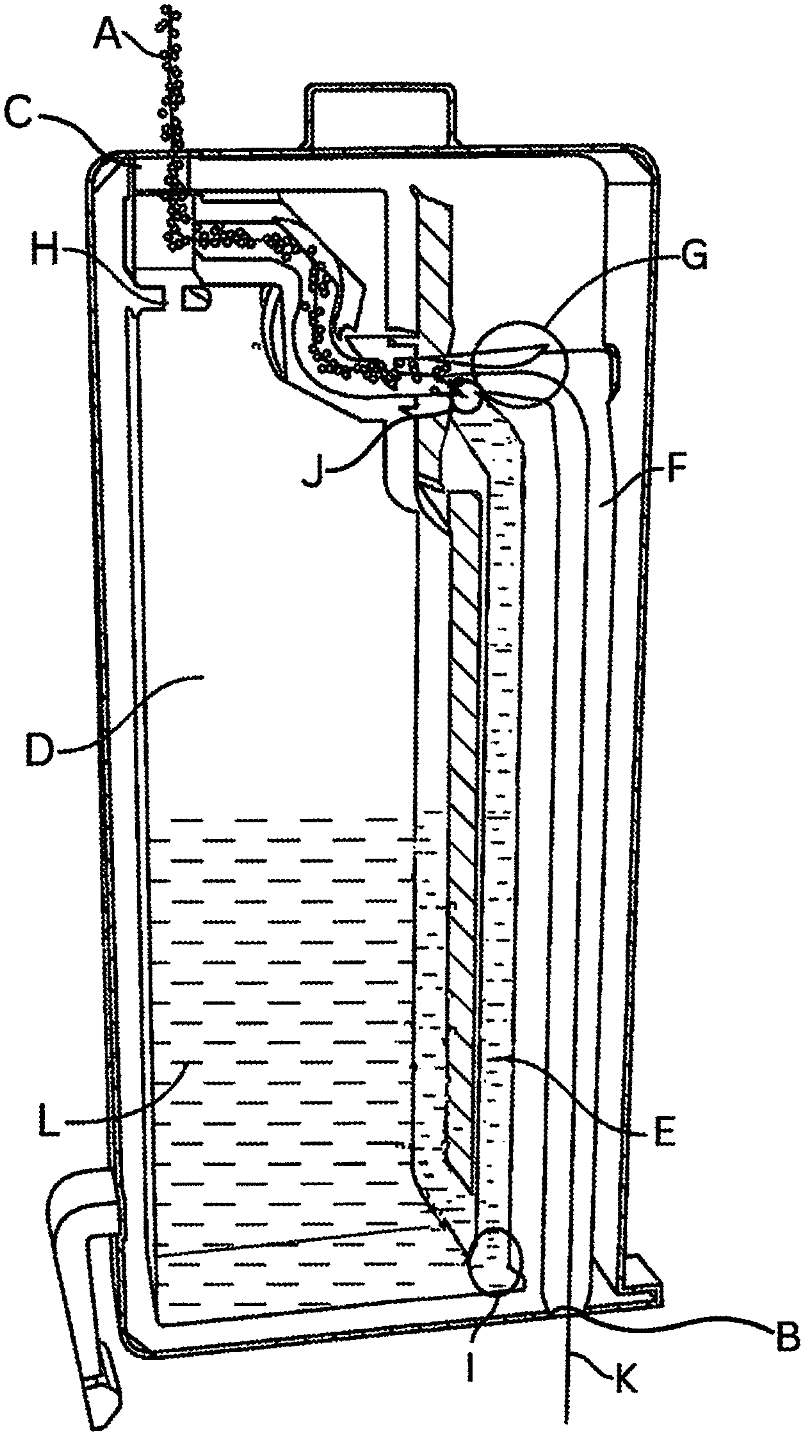
FIG. 1 illustrates a cross-section interior view of a cartridge for fluid dispersal powered by a compressed air tank or an air compressed using an electric motor or pump.

Another example of a device powered by compressed gas includes those described in U.S. application Ser. No. 18/733,625, which is also a cartridge for fluid dispersal. This device is similar to that described in U.S. Pat. App., Pub. Nos. 2023-0264214 and 2023-0263970, and shown in FIG. 1, except: the atomized liquid exits into the liquid reservoir very close to the point of its formation; the cartridge includes a dispersal rate adjuster element, to modify the amount of atomized vapor traveling to the atomization outlet; and the atomization outlet is modified to accommodate a screw cap. The outlet only extends long enough to receive a cap, about 8 mm or less, and has threading for a screw cap.

The cartridge diffusers described in U.S. Pat. App., Pub. Nos. 2023-0264214 and 2023-0263970, as well as U.S. application Ser. No. 18/733,625, are for use in a computer-controlled machine having a set of cartridges in a manifold, powered with an air pressure of 7 to 30 PSI using a high AC current with a 1.5 A pump, providing air movement of about 9150 $in^3$/min. The machines provide air pressure into multiple cartridges at the same time. This is part of their design function, to be like "notes" in a piano. From 1 at a time, to 3, or 4, to as many as 6 and even 12 cartridges may be emitting all at once. Air pressure is proportionally less the more cartridges are used concurrently, and additional air pressure may be needed as more cartridges are uses simultaneously.

The present application addresses the need for a human powered personal fluid inhalation device, which does not heat the fluid, and is powered solely by suction from a person's mouth. The device is configured for human mouth powered operation. The average person generates suction pressures in the range of −10 to −25 cm $H_2O$ when inhaling through devices like a vape pen, cigar, or cigarette; this range translates to approximately −0.14 to −0.36 PSI (negative pressure relative to atmospheric pressure). Suction pressure is typically low because the human respiratory system did not evolve to create high vacuums, or sustain suction for extended periods of time. This is quite different from the cartridge diffusers described above which operate with a pump at a pressure of 7 to 30 PSI continuously. Other devices are powered by compressed air or a propellant, by a hand powered pump, or by heating the liquid with a heating element using electricity. Some nicotine inhalers, such as the NICOTROL® inhaler (see, for example, U.S. Pat. Nos. 4,284,089; 4,793,366; 4,800,903; 4,917,120; 5,167,242; and 5,400,808) form a vapor or gas which contains nicotine for consumption by a user. Accordingly, the problem addressed by the present application is entirely different than that addressed by the references described above.

The present invention includes a fluid inhalation device, which provides a fluid-air mixture to the user, when the device is powered by mouth suction of the user. No other power source is needed to operate the device. When mouth suction is used to power the device, a stream of air enters the device through an air inlet, travels through an air duct and into a nozzle. Within the nozzle, the reduced pressure created by the flowing air sucks liquid from a fluid reservoir through a vacuum channel. Within the nozzle, the liquid is broken up into droplets, and flows out of the nozzle. The flowing air transports the droplets up and through the fluid-air outlet and into the user's mouth, thereby delivering the fluid to the user. Large droplets and bulk liquid are too heavy to be transported out of the device by the moving air, and return back into the fluid reservoir. The device is configured to be used in an upright position, so that the liquid remains at the bottom of the fluid reservoir; the operation of the device makes use of gravity to contain liquid in desired locations, such as at the bottom of the fluid reservoir. In a variation, the nozzle exit directly opens into the fluid reservoir, for example above the level of the liquid contained therein. In a variation, a spray shield is used to intercept large droplets to prevent them from traveling into the user's mouth, for example in the fluid reservoir, or present between the nozzle exit and the fluid-air outlet, or the spray shield may block a straight line between the nozzle exit and the fluid-air outlet. In a variation, a fluid-air mixture channel is used to increase the distance between the nozzle and the fluid-air outlet, for example by connecting the nozzle or the fluid reservoir to the fluid-air outlet, making use of gravity to prevent large droplets from traveling into the user's mouth. In a variation, a mouth piece contains the fluid-air mixture outlet. In a variation, the nozzle exit opens into the fluid-air mixture channel. Each of these variations may be used alone, or in combinations and permutations.

An important advantage of the fluid inhalation devices described in the present application is that the fluid is delivered to the user without heating, as occurs in vaping devices. By avoiding heating, there is no damage or chemical change to the components of the liquid, not only preventing destruction of the ingredients, but also avoid the formation of undesirable, bad-tasting or dangerous chemicals, for example carbon monoxide, nitrogen oxides, carbon dioxide, nitrosamines, aldehydes, and volatile organic compounds (VOCs). The fluid inhalation devices may be manufactured completely out of plastic using, for example, additive manufacture, and thus may avoid introducing metal into the fluid-air mixture inhaled by the user.

Figure 2:
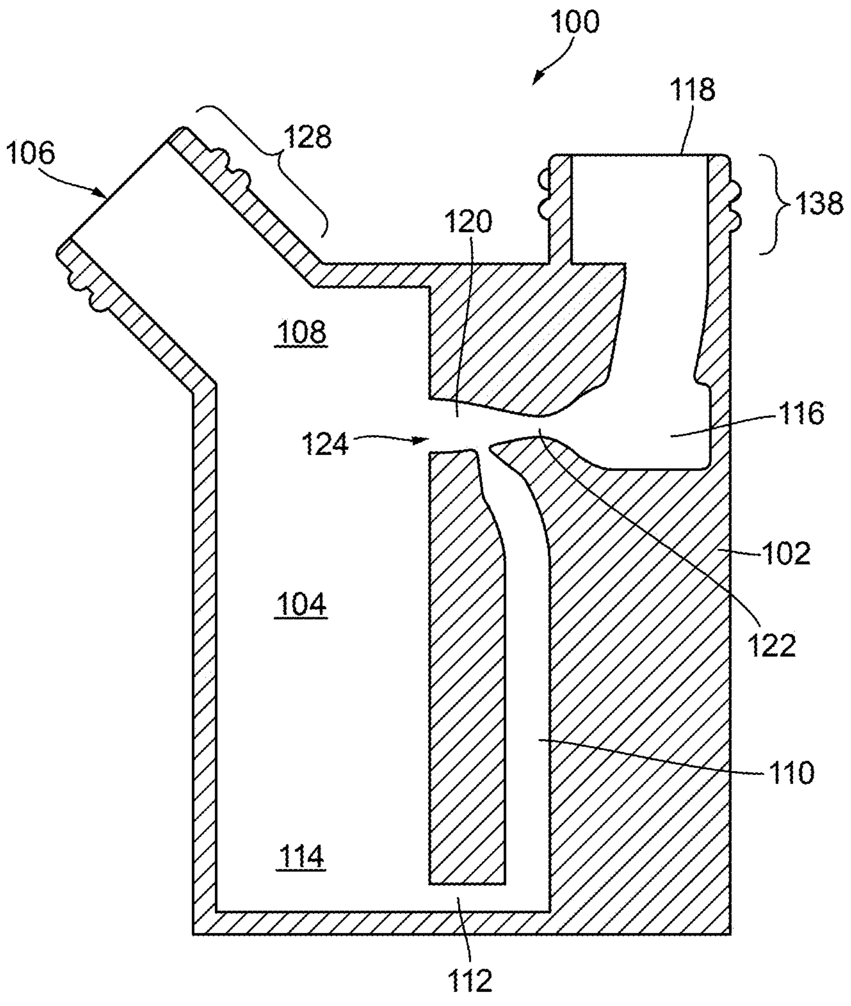
FIG. 2 illustrates a cross-section interior view of a first fluid inhalation device.

FIG. 2 illustrates a cross-section interior view of a first fluid inhalation device, 100, having a casing, 102. The casing has formed therein a fluid reservoir, 104, a fluid-air outlet, 106, a vacuum channel, 110, an air duct, 116, having an air inlet, 118, at a first air duct end, and a nozzle, 120. The fluid-air outlet is connected to a top end, 108, of the fluid reservoir. A bottom end, 112, of the vacuum channel is connected to a bottom end, 114, of the fluid reservoir. The nozzle, 120, includes a nozzle throat, 122, and a nozzle exit, 124, with the nozzle throat being connected to a second air duct end, and the nozzle exit being connected to the fluid reservoir. A top end of the vacuum channel is connected to the nozzle. Preferably, the nozzle throat is narrower than the nozzle exit, and preferably the nozzle exit directly opens into the fluid reservoir, as shown in the figure. Also illustrated are the optional mouth piece, 128, and the optional air inlet stem, 138.

In use, the fluid inhalation device of FIG. 2 contains a liquid in the fluid reservoir. A person (or user) then sucks in air from the fluid-air outlet, using their lips to make a seal around the fluid-air outlet, preferably with the assistance of the optional mouth piece. This suction causes air to flow through the device, entering through the air inlet, traveling through the air duct and through the nozzle. The flowing air has a lower pressure than the ambient air, causing the liquid in the fluid reservoir to flow up through the vacuum channel and into the nozzle. Within the nozzle, the liquid (which may have vaporized in part, due to the reduced pressure within the nozzle) will form a fluid-air mixture and flow out of the nozzle through the nozzle exit and into the fluid reservoir. The fluid-air mixture with then flow out of the top of the fluid reservoir and out of the fluid inhalation device through the fluid-air outlet, into the mouth of the person. The fluid-air mixture will travel through the mouth, and depending on the depth of inhalation by the person, through their throat and into their lungs.

Preferably, the top end of the vacuum channel is connected to the nozzle between the nozzle throat and the nozzle exit. Preferably, the nozzle exit is between the fluid reservoir bottom end and the fluid reservoir top end. Preferably, the nozzle throat is narrower than the air duct where the air duct connects to the nozzle throat.

Preferably, the composition of the liquid is such that most or all of the liquid remains as a liquid, and is contained in the fluid reservoir when the device is held for use with the bottom of the fluid reservoir closest to the ground. The liquid will atomize, forming droplets of various sizes. The smaller droplet will be carried by the air flow through and out of the device and into the user. The larger droplet, in contrast, having a smaller ratio of surface area to volume, will fall and flow to the bottom of the fluid reservoir, or impact the interior walls of the casing, and flow to the bottom of the fluid reservoir. As shown in FIG. 2, the device is configured to provide a very fine mist of the fluid into the mouth of the user when a person uses normal breath inhalation, without the user receiving large droplets or bulk liquid which would be experienced as if a liquid were being sucked into the mouth. Preferably, as shown in FIG. 2, the air inlet is at the top of the fluid inhalation device.

Figure 3:
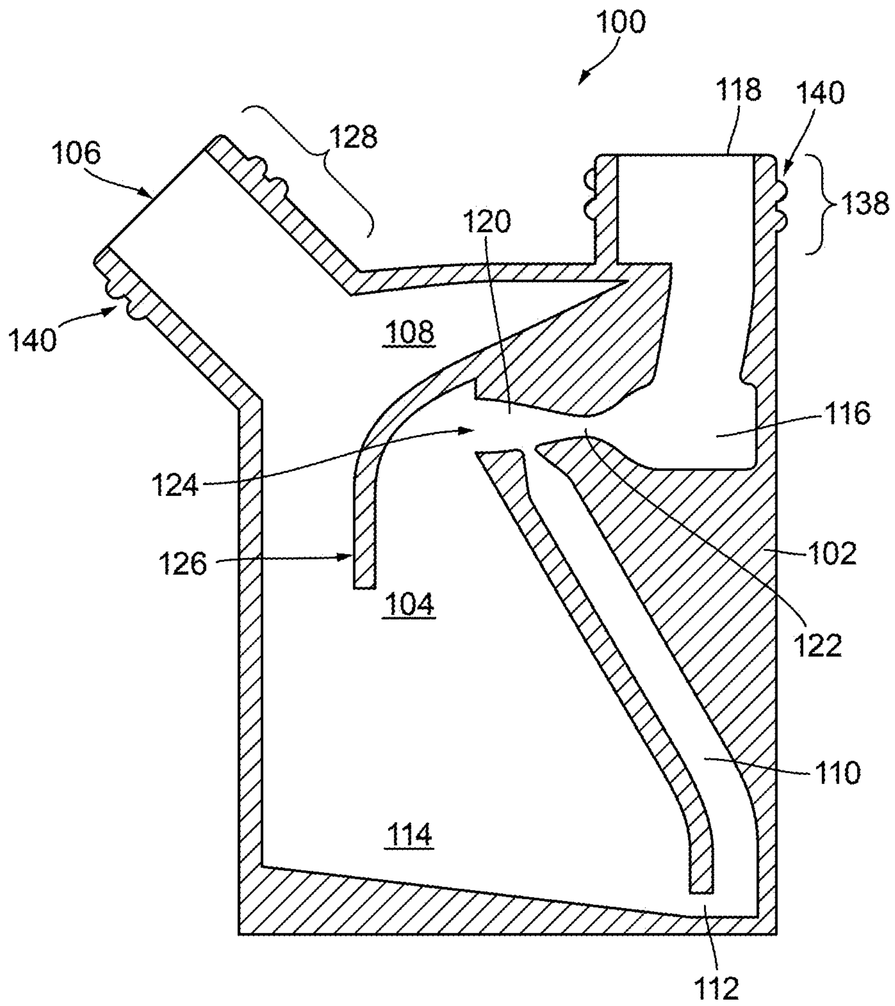
FIG. 3 illustrates a cross-section interior view of a second fluid inhalation device.

FIG. 3 illustrates a cross-section interior view of a second fluid inhalation device, 100. This device is the same as that illustrated in FIG. 2, except the device includes additional features: an optional spray shield, 126, and an optional sloping fluid reservoir bottom. The spray shield provides 2 different functions: the spray shield intercepts the largest droplet exiting the nozzle, causing the largest droplet to flow back to the bottom of the fluid reservoir; and the spray shield elongates the flow path, from the nozzle exit to the fluid-air outlet, and causes the flow path to curve, providing more time and opportunity for the largest droplets to fall and/or impact the interior walls of the casing. The sloping fluid reservoir bottom enhances the amount of liquid in the fluid reservoir which is available to be sucked into the vacuum channel.

Figure 4:
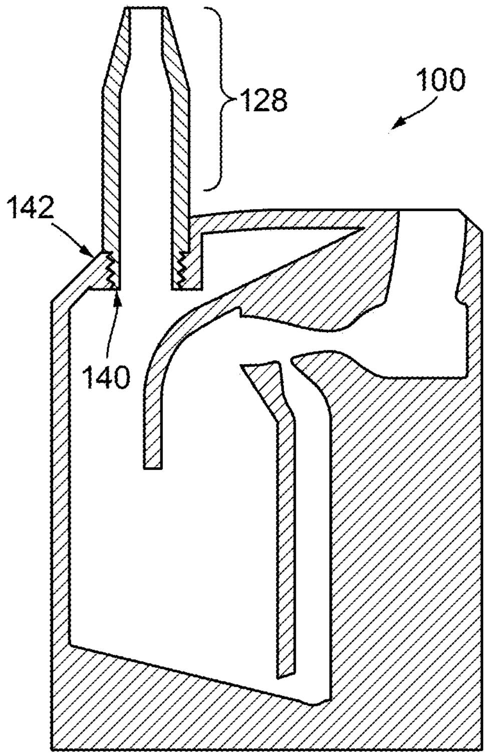
FIG. 4, FIG. 5 and FIG. 6 each illustrate cross-section interior views of additional variations of the fluid inhalation device.
Figure 5:
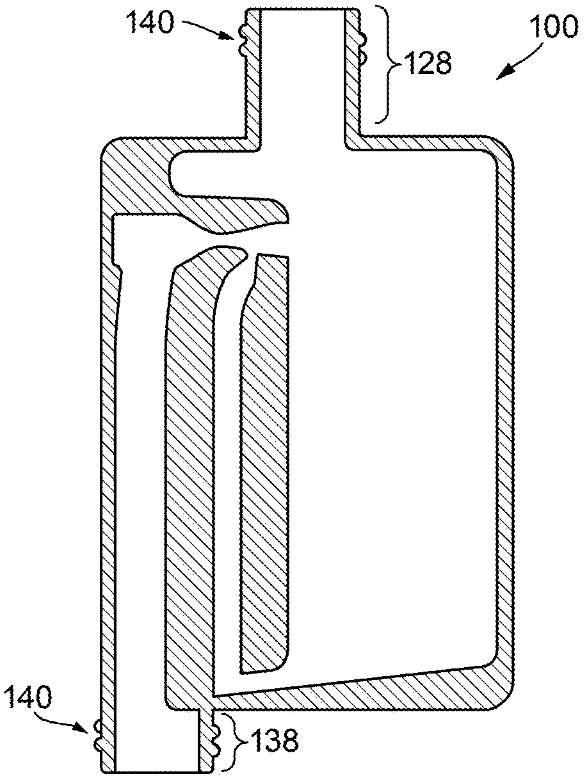
Figure 6:
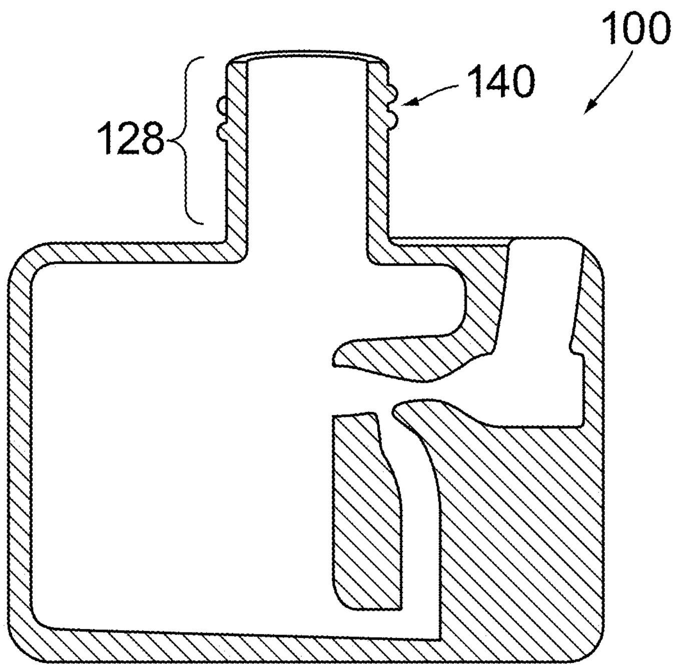

FIG. 4, FIG. 5 and FIG. 6 illustrate additional cross-section interior views of variations of the fluid inhalation device, 100. In FIG. 4, a different shape is used for the mouth piece. Furthermore, in contrast to the monolithic device illustrated in FIG. 2, the mouth piece is FIG. 3 is a separate part, having external threads, 140, which are screwed into the internal threads, 142, allowing for attachment of the mouth piece to the body of the fluid inhalation device. As illustrated in both FIG. 2 and FIG. 5, both the mouth piece and the air inlet stem includes external threads. Furthermore, the device of FIG. 4 also has an air inlet which opens out of the bottom of the device. FIG. 6, similar to FIG. 5, has the mouth piece containing the fluid-air outlet centered on the top face of the casing. Preferably, the air inlet is located on the side surfaces, and more preferably located on the top surface of the fluid inhalation device to help prevent leakage, and avoid any protrusions or irregularity which would prevent standing the device up right on a flat surface, such as a table or a desk. Preferably, the bottom surface of the fluid inhalation device is flat, to allow for standing the device up right on a flat surface.

Figure 7:
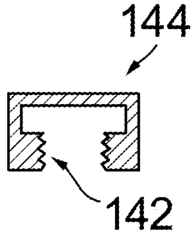
FIG. 7, FIG. 8, FIG. 9 and FIG. 10 each illustrate different types of closures for sealing the fluid-air outlet and/or the air inlet of various fluid inhalation devices.
Figure 8:
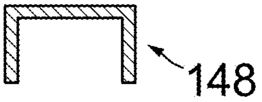
Figure 9:
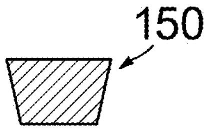
Figure 10:
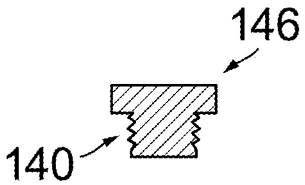

FIG. 7, FIG. 8, FIG. 9 and FIG. 10 illustrate different types of closures for sealing the fluid-air outlet and/or the air inlet of various fluid inhalation devices, such as a mouth piece cap or a fluid inlet cap. FIG. 7 shows a cap with interior thread, 144, the interior threads being configured to mate with the exterior threads of the mouth piece and/or the air inlet extension, such as those shown in FIG. 2, FIG. 3, FIG. 5 and FIG. 6. FIG. 8 shows a snap cap, 148, configured to snap over and seal a mouth piece and/or an air inlet extension, such that threads are not required. FIG. 9 illustrates a stopper 150, made of flexible and/or elastomeric material, which may be inserted into a fluid-air outlet or air inlet for sealing. FIG. 10 shows a cap with external threads, 146, which is configured to seal a fluid-air outlet having internal threads, such as the device shown in FIG. 4 (in which case the mouth piece is removed to allow for screwing in the cap with external threads and sealing the fluid-air outlet). With each of these different closures, attachment to the fluid inhalation device allows for formation of a liquid tight seal, to prevent any leakage of liquid contained in the fluid inhalation device from leaking out while the device is not in use, and may be transported or held on its side, or even upside-down.

Figure 11A:
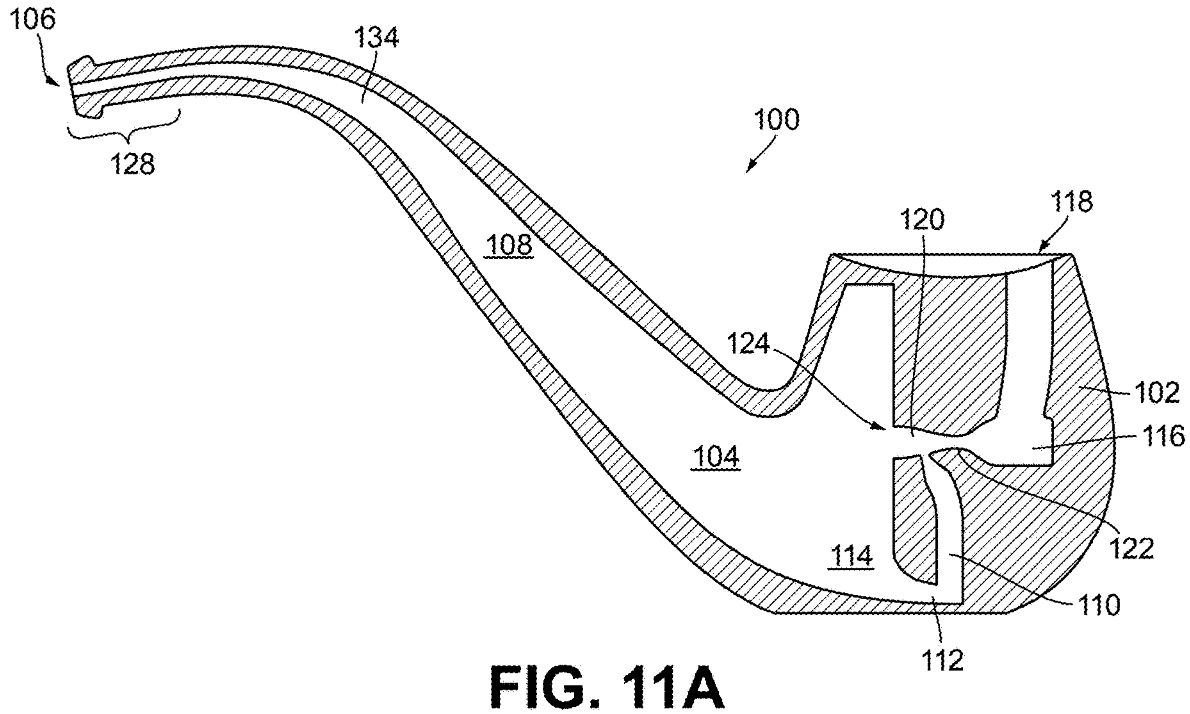
FIG. 11A and FIG. 11B illustrates different cross-section interior views of a variation of a fluid inhalation device which is styled to have the same shape as a classic tobacco pipe.
Figure 11B:
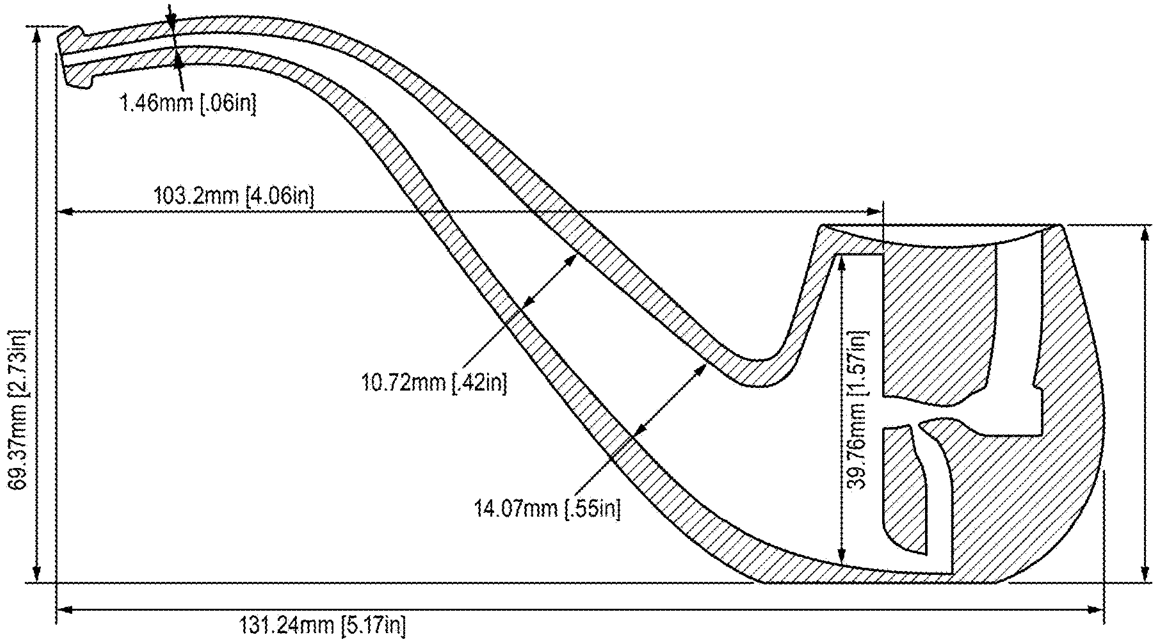

FIG. 11A illustrates another cross-section interior view of a variation of a fluid inhalation device which is styled to have the same shape as a classic tobacco pipe. As show, the fluid inhalation device, 100, includes fluid-air mixture channel, 134, which connects the fluid reservoir top end, 108, with the fluid-air outlet, 106. The optional fluid-air mixture channel provides the same functions as does the optional spray shield: the fluid-air mixture channel intercepts the largest droplet exiting the nozzle, causing the largest droplet to flow back to the bottom of the fluid reservoir; and the fluid-air mixture channel elongates the flow path, from the nozzle exit to the fluid-air outlet, and optionally causes the flow path to curve, providing more time and opportunity for the largest droplets to fall and/or impact the interior walls of the casing. FIG. 11B illustrates the same device as FIG. 11A, except with dimensions of the various features of the device, to provide a fluid inhalation device configured to provide atomized liquid to a user.

Figure 12:
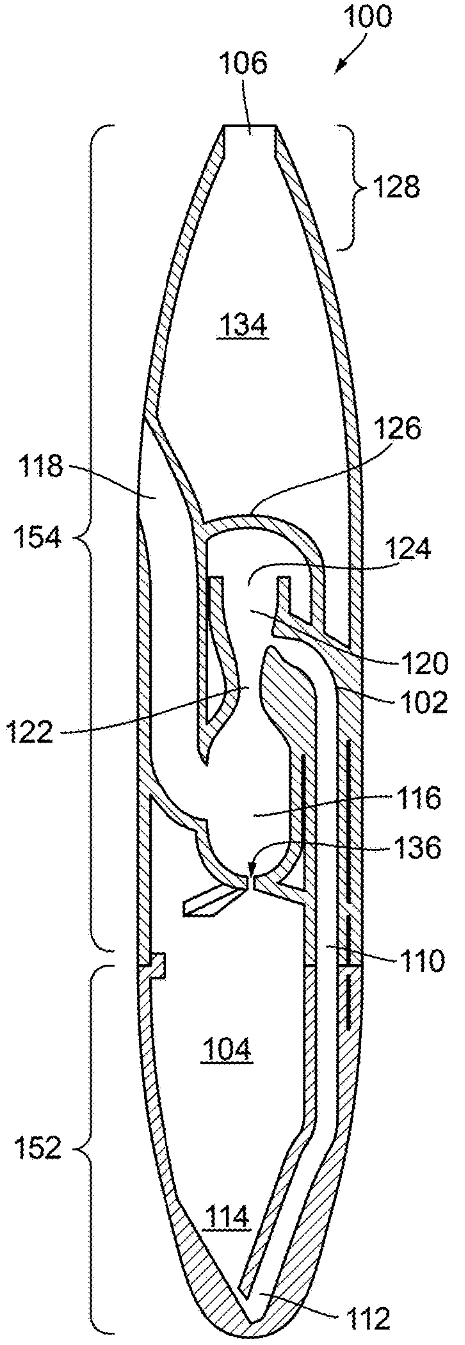
FIG. 12 and FIG. 13 illustrate 2 perpendicular cross-section interior views of another variation of a fluid-inhalation device.
Figure 13:
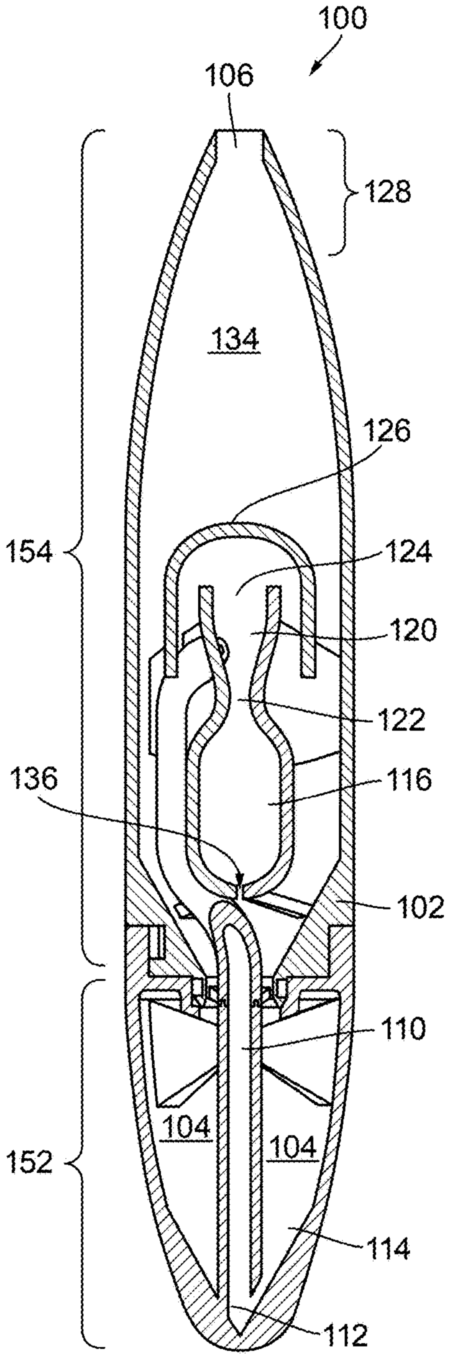

FIG. 12 and FIG. 13 illustrate 2 perpendicular cross-section interior views of another variation of a fluid-inhalation device. Unlike the devices illustrated the prior figures, the nozzle, 120, of the fluid inhalation device, 100, does not open directly into the fluid reservoir, 104, but rather points upwards and is above the fluid reservoir, placed in a fluid-air mixture channel, 134, which connects the fluid reservoir and the fluid-air outlet, 106. The spray shield, 126, has a cup-shape and covers the nozzle exit, 124. Larger droplets which intersect with the spray shield will run down the outer edges of the spray shield and flow back into the fluid reservoir. A liquid which flows into the nozzle from the vacuum channel, 110, which is not atomized, or which is in the form of large droplets which fall down, will flow or fall back into the air duct, and will be returned to the fluid reservoir through a fluid return channel, 136. As shown in FIGS. 12 and 13, the fluid inhalation device is formed of a removable reservoir, 152, which couples to a removable top, 154; as shown, the removable reservoir and removable top snap together.

The mouth piece has a size and length such that the mouth piece is configured to allow a user to insert the mouth piece in the mouth and form a seal, both liquid and gas tight, with the user's lips. A mouth piece has a length of at least 1 cm, preferably at least 1.5 cm, more preferably at least 2 cm. A mouth piece may be at most 6 cm, more preferably at most 5 cm, most preferably at most 4 cm, for example 1 to 6 cm, or 1.5 to 5 cm, or 2 to 4 cm, in length. The mouth piece may be circular, but preferably it has a non-circular cross-section, such as an elliptical cross-section shape, or a flat shape, for a more comfortable fit within the mouth. In some designs with a circular cross-section, threads may be included at the end of the mouth piece to allow for a screw cap to seal the device. The opening in the mouth piece preferably has an area of at most 0.75 $cm^2$, more preferably at most 0.25 $cm^2$, even more preferably at most 0.1 $cm^2$ (100 $mm^2$), and even more preferably at most 50 $mm^2$, for example 1 to 100 $mm^2$, 5 to 50 $mm^2$, including 5, 6, 8, 10, 12, 15, 20, 25, 30, 40 and 50 $mm^2$, and all ranges therebetween.

Figure 14:
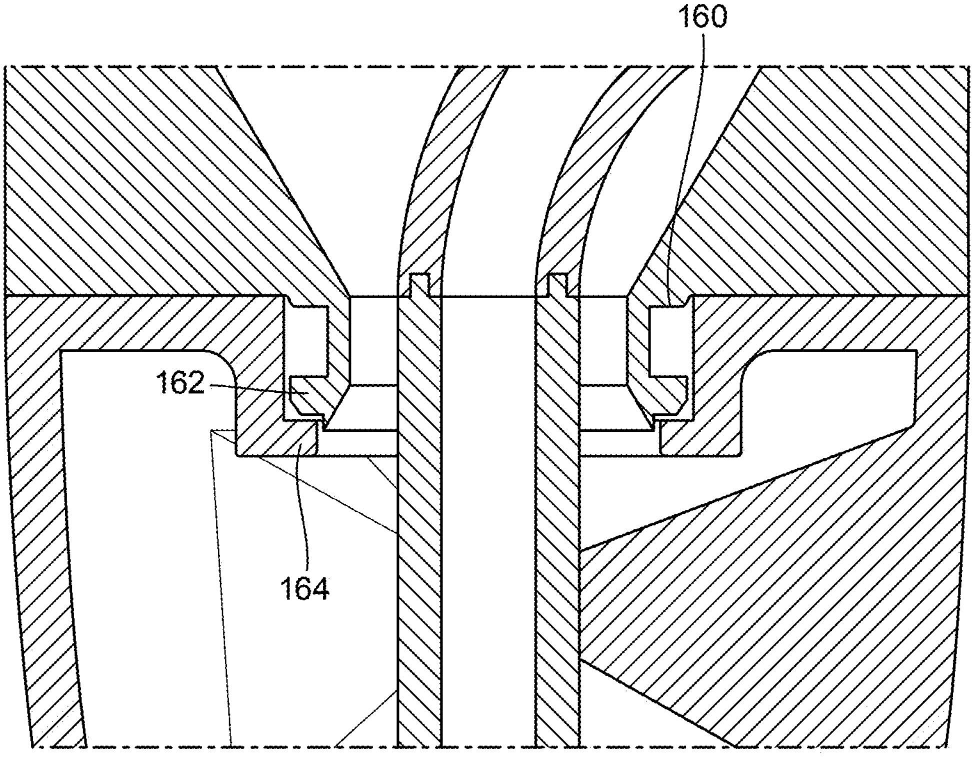
FIG. 14 illustrated in cross-section interior view of a snap together mechanism.
Figure 15:
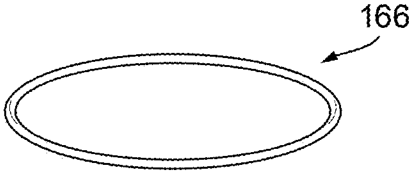
FIG. 15 shows an optional O-ring
Figure 16:
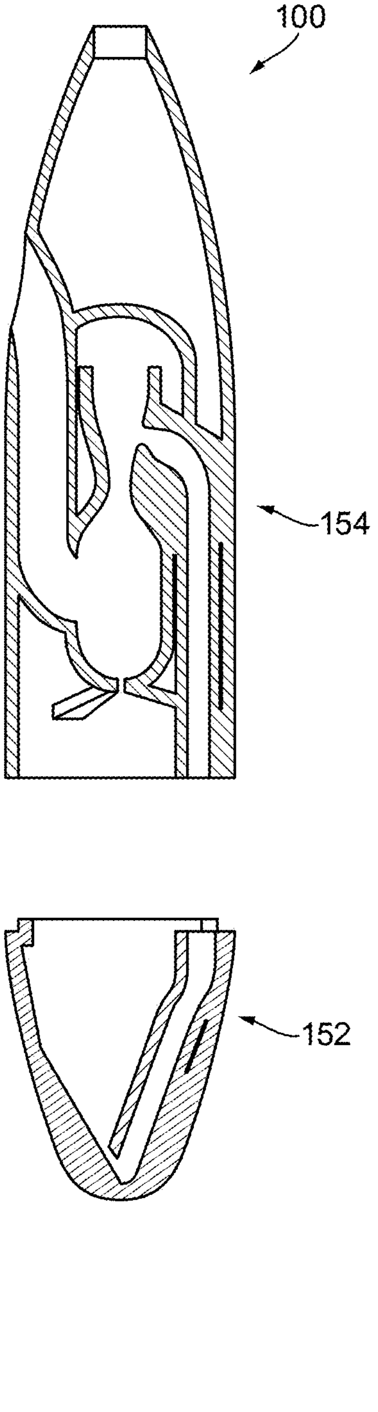
FIG. 16 illustrates cross-section interior views of the removable reservoir and the removable top, separated from each other.

Details of the snap together mechanism of the device shown in FIG. 12 and FIG. 13 are illustrated in cross-section interior view in FIG. 14. The snap together mechanism includes an O-ring groove, 160, an alignment notch, 162, and a sealing surface, 164. An optional O-ring, 166, shown in FIG. 15, is omitted from FIG. 14, for clarity. The mechanism is configured to provide a sufficiently tight seal to prevent any liquid from leaking out of the device, and a gas tight seal so that the device operates properly. The inclusion of the optional O-ring may be used to improve the tightness of the seal, as needed; it is formed of an elastomeric material, and may be placed into the O-ring groove prior to assembly of the fluid inhalation device. Cross-section interior views of the removable reservoir and the removable top, separated from each other, is shown in FIG. 16.

Figure 17:
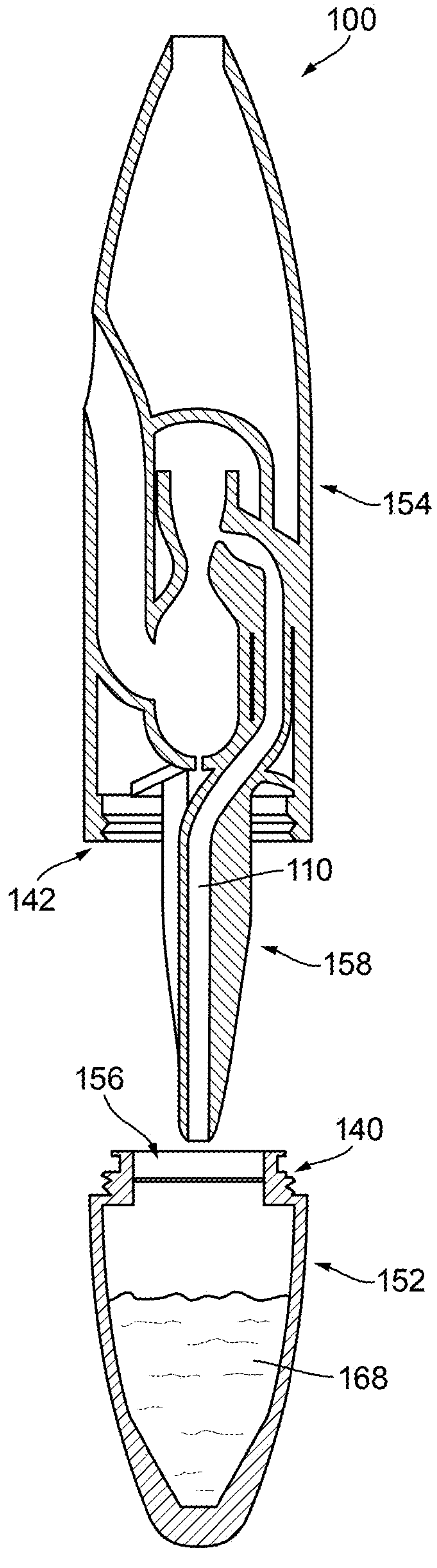
FIG. 17 illustrates a cross-section interior view of an alternate design of a fluid inhalation device including a removable reservoir and a removable top.

An alternate design of a fluid inhalation device including a removable reservoir and a removable top, is shown in cross-section interior view in FIG. 17. The fluid inhalation device, 100, includes a removable reservoir, 152, and a removable top, 154. The removable reservoir optionally contains a fluid, 168, and a breakable seal, 156, which maintains the fluid within the removable reservoir prior to assembly of the fluid inhalation device. At an upper end of the removable reservoir are external threads, 140. The removable top includes stem, 158, having contained therein the lower portion of the vacuum channel, 110. At the lower end of the removable top are internal threads, 142. To assemble the fluid inhalation device, the external threads of the removable reservoir are screwed into the internal threads of the removable top, the action of which causes the stem to pierce the breakable seal, allowing the vacuum channel to access the fluid. The external threads and the internal threads are configured to provide a sufficiently tight seal to prevent any liquid from leaking out of the device, and a gas tight seal so that the device operates properly.

Figure 18:
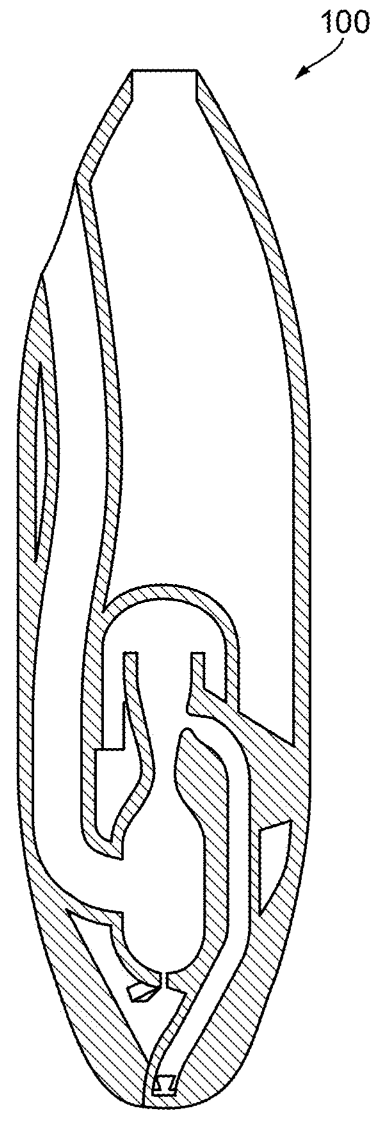
FIG. 18 illustrates a cross-section interior view of an alternate design of a fluid inhalation device which is monolithic (or has a unibody construction).

An alternate design of a fluid inhalation device which is monolithic (or has a unibody construction) is shown in cross-section interior view in FIG. 18. Optionally, a one-way valve, such as a simple thin flap of plastic, may be included in the air duct, and at the air inlet, to help prevent liquid from leaking out of the device when not in used and not held in an upright position.

In a variation, the fluid inhalation device includes means for producing a fluid-air mixture, for example the vacuum channel together with the nozzle. In a variation, the fluid inhalation device includes means for providing a stream of air into the device, for example the air inlet together with the air duct. In a variation, the fluid inhalation device includes means for returning large droplets and bulk fluid from the fluid-air mixture to the fluid reservoir, for example the nozzle exit or other element for producing the fluid-air mixture opening into the fluid reservoir, alternatively a fluid return channel. In a variation, the fluid inhalation device includes means for providing the fluid-air mixture to the fluid-air outlet, such as a connection between the nozzle exit and the fluid-air outlet. In a variation, the fluid inhalation device includes means for preventing large droplets from reaching the fluid-air outlet, for example a spray shield or fluid-air mixture channel.

The fluid inhalation device is configured to deliver an atomized liquid (alone or mixed with vapor from the liquid) containing one or more agents including phytochemicals, terpenes, psychoactive agents, drugs, nutraceuticals, plant extract, fragrances, flavorings, and other desirable agents, or mixtures thereof, to the mouth, tongue, throat, or lungs of a user. Examples of such agents includes terpenes such as CBD, THC, and limonene; alkaloids such as nicotine; flavorings such as menthol and vanillin; plant extracts including cannabis extracts; psychoactive agents such as ethanol and caffeine; nicotine fluids, essential oils, plant isolate fluids, cannabis fluids, and any ingredients thereof; and drugs such as steroids, bronchodilators (such as albuterol), stimulants, decongestants, vasoconstriction agents, antibiotics, anesthetics and NSAIDs. The compositions are preferably liquid with a concentration chosen to deliver the desired amount to the user. For example, the liquids currently used with vaping devices, such as those which contain nicotine and/or cannabinoids (such as CBD and THC), may be used in the fluid inhalation device. The concentration of nicotine in the liquid may be 3 mg/ml to 20 mg/ml. The concentration of CBD and/or THC may be 1 mg/ml to 50 mg/ml. Other agents, such as those described above, may be present in the liquid at a concentration of, for example, 0.1 mg/ml to 100 mg/ml.

Carriers and additives which may be present in the liquids for use with the fluid inhalation device include water; alcohols such as ethanol; glycols such as propylene glycol; sweeteners (including sugars such a sucrose, fructose, glucose and xylitol); glycerin; vegetable oils; salts such as sodium chloride; pH adjusting agents such as acetic acid and sodium bicarbonate; pharmaceutically acceptable excipients and carriers; ingredients commonly used in vaping fluids; other agents which are generally regarded as safe (GRAS); Class 3 solvents listed in "ICH guidance for industry Q3C Impurities: Residual Solvents" and mixtures and combinations thereof. Preferred components of the liquid include 1-butanol, 1-pentanol, 1-propanol, 2-butanol, 2-methyl-1-propanol, 2-propanol, 3-methyl-1-butanol, acetaldehyde, acetic acid, acetoin, acetone, alcohols, anisole, benzaldehyde, butyl acetate, carvone, cinnamaldehyde, decanal, diacetyl, dimethyl sulfoxide, ethanol, ethyl acetate, ethyl butyrate, ethyl ether, ethyl formate, ethyl vanillin, eugenol, formic acid, fructose, glucose, glycerin, glycols, heptane, isobutyl acetate, isopropyl acetate, limonene, linalool, methyl acetate, methyl ethyl ketone, pentane, propyl acetate, propylene glycol, salts, sodium bicarbonate, sodium chloride, sucrose, sugars, sweeteners, tert-butyl methyl ether, tocopherol acetate, triacetin, triethylamine, vegetable oils, water, xylitol, and mixtures of 2, 3, 4, 5 or 6, or more thereof; each of which may be present in an amount by weight of 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98 and 99%, including all ranges therebetween for each component. Preferably, the liquid composition also contains nicotine and/or cannabinoids (preferably, CBD and/or THC, such delta-9-THC and/or delta-8-THC).

The device may be made by additive manufacturing (often referred to as 3-D printing), from different materials including plastics (such as nylon, polyethylene, polypropylene, epoxy, polyurethanes, polystyrenes, polycarbonate, copolymers and combinations thereof), metals such as aluminum, ceramics and glass, and combinations thereof. Injection molding may also be used if the device is prepared as a set of components designed for injection molding and then assembled. Combinations of these manufacturing methods may also be used. Additive manufacturing may result in a monolithic device with all parts being a single unibody construction. Alternatively, individual parts, such as the mouth piece, may be made as an attachment to the device by matching threads, with an adhesive, or by thermal bonding in the case of thermoplastic construction.

A typical human male has a breath volume of about 0.5 liters (tidal volume), and so the device is configured to operate on a smaller volume of air sucked in through the fluid inhalation device. The inhalation may last less than 1 second, or may be controlled to last several seconds, including 1, 2, 3, 4, 5, 6, 7, 8, 9 or 10 seconds. The fluid inhalation device is configured for human mouth powered operation, that is operated by suction by mouth on a mouth piece at a pressure of −0.14 to −0.36 PSI, negative pressure relative to atmospheric pressure. The amount of fluid delivered to the mouth of a user by such human powered operation for a period of 1 second, is preferably 0.001 to 0.01 ml, more preferably 0.002 to 0.008 ml, most preferably 0.004 to 0.006 ml. Typical inhalation time by a user is 1 to 3 seconds. In the case of nicotine or cannabinoids, preferably the concentration of the nicotine or cannabinoids in the liquid is adjusted so that 10-18 inhalation from the device would deliver 1.0-1.8 mg of nicotine or cannabinoids to the user. This would mimic the dosage received from smoking tobacco products or cannabis products. In the case of nicotine, 1 ml of fluid should mimic the dosage received by a user when smoking a 20-cigarette pack.

According to Stokes" law, the drag force F on a sphere of radius r moving through a fluid of viscosity n at speed v is given by: $F=6\pi\eta rv$. Although several assumptions underlie the validity of the Stokes' law, it provides a good approximation for small droplets flowing through a fluid inhalation device under the effects of flowing air caused by human inhalation. The drag force is directly proportional to the radius of the droplet. The effects of gravity, and the momentum of the sphere, are proportional to the mass of the droplet, which for a homogenous liquid is proportional to the volume V of the droplet, which $V=4/3\pi r^3$. Furthermore, if the liquid in the droplet can evaporate under the ambient conditions, which is true for water and ethanol, the size of the droplet will shrink after formation. Droplet size in air or another gas may be measured using light scattering. Preferably, 90% of the droplets which flow through the fluid inhalation device, just prior to exiting the device have a radius of at most 100 μm, more preferably at most 50 μm, even more preferably at most 30 μm; for example, 90% of the droplets may have a radius of at most 100, 90, 80, 70, 60, 50, 40, 30, 20, 10, 5 or 1 μm, including all values and ranges therebetween.

What is claimed is:

1. A fluid inhalation device, comprising:
a casing having therein
  a fluid reservoir, having
    a top end and
    a bottom end,
  a fluid-air outlet connected to the top end of the fluid reservoir,
  a nozzle, having
    a nozzle exit connected to the fluid reservoir, and
    a nozzle throat,
  a vacuum channel, having
    a bottom end connected to the bottom end of the fluid reservoir, and
    a top end connected to the nozzle,
  an air duct, having
    an air inlet at a first air duct end, and
    a second air duct end connected to the nozzle throat, and
  a mouth piece, containing the fluid-air outlet,
wherein the nozzle throat is narrower than the nozzle exit, and
when fluid is present in the fluid reservoir, the fluid inhalation device delivers 0.001 to 0.01 ml of fluid under suction pressure through the mouth piece without heating and solely powered by mouth of a human user of −0.14 to −0.36 PSI, negative pressure relative to atmospheric pressure, in 1 second, and the suction pressure causes air to enter the air inlet and a fluid-air mixture to exit through the fluid-air outlet.

2. The fluid inhalation device of claim 1, further comprising a fluid return channel connecting the air duct to the fluid reservoir.

3. The fluid inhalation device of claim 1, further comprising a spray shield, between the nozzle exit and the fluid-air outlet.

4. The fluid inhalation device of claim 3, wherein the spray shield is in the fluid reservoir.

5. The fluid inhalation device of claim 3, wherein the spray shield blocks a straight line between the nozzle exit and the fluid-air outlet.

6. The fluid inhalation device of claim 1, wherein the bottom end of the fluid reservoir slopes down toward the vacuum channel bottom end.

7. The fluid inhalation device of claim 1, wherein the top end of the vacuum channel is connected to the nozzle between the nozzle throat and the nozzle exit.

8. The fluid inhalation device of claim 1, wherein the nozzle exit is between the fluid reservoir bottom end and the fluid reservoir top end.

9. The fluid inhalation device of claim 1, wherein the nozzle throat is narrower than the air duct.

10. The fluid inhalation device of claim 1, comprising:
a removable top containing the fluid-air outlet, and
a removable reservoir containing at least a portion of the fluid reservoir,
wherein the removable top and the removable reservoir are adapted to attach together.

11. The fluid inhalation device of claim 1, further comprising the fluid in the fluid reservoir,
wherein the fluid has a volume of 0.5 to 5 ml, and
the fluid comprises:
(a) at least one member selected from the group consisting of 1-butanol, 1-pentanol, 1-propanol, 2-butanol, 2-methyl-1-propanol, 2-propanol, 3-methyl-1-butanol, acetaldehyde, acetic acid, acetoin, acetone, alcohols, anisole, benzaldehyde, butyl acetate, carvone, cinnamaldehyde, decanal, diacetyl, dimethyl sulfoxide, ethanol, ethyl acetate, ethyl butyrate, ethyl ether, ethyl formate, ethyl vanillin, eugenol, formic acid, fructose, glucose, glycerin, glycols, heptane, isobutyl acetate, isopropyl acetate, limonene, linalool, methyl acetate, methyl ethyl ketone, pentane, propyl acetate, propylene glycol, salts, sodium bicarbonate, sodium chloride, sucrose, sugars, sweeteners, tert-butyl methyl ether, tocopherol acetate, triacetin, triethylamine, vegetable oils, water and xylitol, and
(b) at least one member selected from the group consisting of nicotine, THC and CBD.

12. The fluid inhalation device of claim 1, wherein the fluid inhalation device is monolithic.

13. A fluid inhalation device, comprising:
a casing having therein
a fluid reservoir, having
a top end and
a bottom end,
a fluid-air outlet connected to the top end of the fluid reservoir,
a nozzle, having
a nozzle exit connected to the fluid reservoir, and
a nozzle throat,
a vacuum channel, having
a bottom end connected to the bottom end of the fluid reservoir, and
a top end connected to the nozzle,
an air duct, having
an air inlet at a first air duct end, and
a second air duct end connected to the nozzle throat,
a mouth piece, containing the fluid-air outlet,
a spray shield, between the nozzle exit and the fluid-air outlet, and
a fluid-air mixture channel connecting the fluid reservoir to the fluid-air outlet,
wherein the nozzle throat is narrower than the nozzle exit, the nozzle exit directly opens into the fluid-air mixture channel, and
when fluid is present in the fluid reservoir, the fluid inhalation device delivers 0.001 to 0.01 ml of fluid under suction pressure through the mouth piece without heating and solely powered by mouth of a human user of −0.14 to −0.36 PSI, negative pressure relative to atmospheric pressure, in 1 second, and the suction pressure causes air to enter the air inlet and a fluid-air mixture to exit through the fluid-air outlet.

14. The fluid inhalation device of claim 13, further comprising a fluid return channel connecting the air duct to the fluid reservoir.

15. The fluid inhalation device of claim 13, wherein the spray shield is in the fluid reservoir.

16. The fluid inhalation device of claim 13, wherein the spray shield blocks a straight line between the nozzle exit and the fluid-air outlet.

17. The fluid inhalation device of claim 13, wherein the bottom end of the fluid reservoir slopes down toward the vacuum channel bottom end.

18. The fluid inhalation device of claim 13, wherein the top end of the vacuum channel is connected to the nozzle between the nozzle throat and the nozzle exit.

19. The fluid inhalation device of claim 13, having:
a removable top containing the fluid-air outlet, and
a removable reservoir containing at least a portion of the fluid reservoir,
wherein the removable top and the removable reservoir are adapted to attach together.

20. The fluid inhalation device of claim 13, further comprising the fluid in the fluid reservoir,
wherein the fluid has a volume of 0.5 to 5 ml, and
the fluid comprises:
(a) at least one member selected from the group consisting of 1-butanol, 1-pentanol, 1-propanol, 2-butanol, 2-methyl-1-propanol, 2-propanol, 3-methyl-1-butanol, acetaldehyde, acetic acid, acetoin, acetone, alcohols, anisole, benzaldehyde, butyl acetate, carvone, cinnamaldehyde, decanal, diacetyl, dimethyl sulfoxide, ethanol, ethyl acetate, ethyl butyrate, ethyl ether, ethyl formate, ethyl vanillin, eugenol, formic acid, fructose, glucose, glycerin, glycols, heptane, isobutyl acetate, isopropyl acetate, limonene, linalool, methyl acetate, methyl ethyl ketone, pentane, propyl acetate, propylene glycol, salts, sodium bicarbonate, sodium chloride, sucrose, sugars, sweeteners, tert-butyl methyl ether, tocopherol acetate, triacetin, triethylamine, vegetable oils, water and xylitol, and
(b) at least one member selected from the group consisting of nicotine, THC and CBD.

21. The fluid inhalation device of claim 13, wherein the fluid inhalation device is monolithic.

22. A set for assembling into a fluid inhalation device, comprising:
(I) a removable reservoir, including
(i) 0.5 to 5 ml of a fluid, and
(ii) a breakable seal, maintaining the fluid within the removable reservoir, and
(II) a removable top, including a fluid-air outlet,
wherein the removable reservoir and the removable top are adapted to attached together to form the fluid inhalation device and configured to break the breakable seal when attached together, and the fluid inhalation device comprises a casing having therein a fluid reservoir including the removable reservoir, and having a top end and a bottom end, the fluid-air outlet connected to the top end of the fluid reservoir, a nozzle, having a nozzle exit connected to the fluid reservoir, and a nozzle throat, a vacuum channel, having a bottom end connected to the bottom end of the fluid reservoir, and a top end connected to the nozzle, an air duct, having an air inlet at a first air duct end, and a second air duct end connected to the nozzle throat, and a mouth piece, containing the fluid-air outlet, wherein the nozzle throat is narrower than the nozzle exit, and when fluid is present in the fluid reservoir, the fluid inhalation device delivers 0.001 to 0.01 ml of fluid under suction pressure through the mouth piece without heating and solely powered by mouth of a human user of −0.14 to −0.36 PSI, negative pressure relative to atmospheric pressure, in 1 second, and the suction pressure causes air to enter the air inlet and a fluid-air mixture to exit through the fluid-air outlet.

23. The set of claim 22, wherein the fluid inhalation device further comprising a fluid return channel connecting the air duct to the fluid reservoir.

24. The set of claim 22, wherein the fluid inhalation device further comprising a spray shield which blocks a straight line between the nozzle exit and the fluid-air outlet.

25. The set of claim 22, wherein the fluid comprises:

(a) at least one member selected from the group consisting of 1-butanol, 1-pentanol, 1-propanol, 2-butanol, 2-methyl-1-propanol, 2-propanol, 3-methyl-1-butanol, acetaldehyde, acetic acid, acetoin, acetone, alcohols, anisole, benzaldehyde, butyl acetate, carvone, cinnamaldehyde, decanal, diacetyl, dimethyl sulfoxide, ethanol, ethyl acetate, ethyl butyrate, ethyl ether, ethyl formate, ethyl vanillin, eugenol, formic acid, fructose, glucose, glycerin, glycols, heptane, isobutyl acetate, isopropyl acetate, limonene, linalool, methyl acetate, methyl ethyl ketone, pentane, propyl acetate, propylene glycol, salts, sodium bicarbonate, sodium chloride, sucrose, sugars, sweeteners, tert-butyl methyl ether, tocopherol acetate, triacetin, triethylamine, vegetable oils, water and xylitol, and (b) at least one member selected from the group consisting of nicotine, THC and CBD.

* * * * *